United States Patent [19]

Antoni et al.

[11] Patent Number: 5,236,586
[45] Date of Patent: Aug. 17, 1993

[54] APPARATUS FOR THE TREATMENT OF FLUIDS

[75] Inventors: Roland Antoni, Senden; Georg Mayer, Hechingen-Boll; Manfred Raff, Bisingen-Thanheim; Kurt Spranger, Ammerbuch; Josef Volm, Haigerloch-Owingen, all of Fed. Rep. of Germany

[73] Assignee: Gambro Dialysatoren GmbH & Co KG, Fed. Rep. of Germany

[21] Appl. No.: 924,320

[22] Filed: Aug. 3, 1992

[30] Foreign Application Priority Data

Aug. 1, 1991 [SE] Sweden ................................ 9102275

[51] Int. Cl.$^5$ .......................................... B01D 63/02
[52] U.S. Cl. ............................ 210/321.8; 210/321.89; 210/500.23
[58] Field of Search ................ 261/DIG. 65; 55/158, 55/16; 210/500.23, 321.6, 321.64, 321.72, 321.71, 321.78, 321.79, 321.8, 321.87, 321.88, 321.89, 321.81, 321.9

[56] References Cited

U.S. PATENT DOCUMENTS

| | | | |
|---|---|---|---|
| 4,381,267 | 4/1983 | Jackson | 261/DIG. 65 |
| 4,724,900 | 2/1988 | Baurmeister et al. | |
| 4,990,251 | 2/1991 | Spranger et al. | |
| 5,002,668 | 3/1991 | Spranger | |

FOREIGN PATENT DOCUMENTS

| | | |
|---|---|---|
| 0305672 | 6/1988 | European Pat. Off. |
| 0442310 | 1/1991 | European Pat. Off. |
| WO8801895 | 3/1988 | PCT Int'l Appl. |

Primary Examiner—Frank Sever
Attorney, Agent, or Firm—Lerner, David, Littenberg, Krumholz & Mentlik

[57] ABSTRACT

Apparatus for the treatment of fluids are disclosed including a cylindrical housing closed at both ends by end caps, one of which includes an inlet for a fluid and the other includes an outlet for the fluid, a plurality of hollow fibers are arranged longitudinally within the housing between a pair of end walls, and one of the end caps includes an outlet for a second fluid which can thus be withdrawn from the outer surface of the hollow fibers between the end walls, and the apparatus includes a ring mounted between the hollow fibers at one of the end caps in order to create a fluid channel for the second fluid between the ring and the inner wall surface of the housing. This apparatus can be used, for example, for hemofiltration, hemodiafiltration or hemodialysis, but it may also be generally used for dialysis or filtration and purification of sewage, and for heat transfer, or as an oxygenator.

11 Claims, 3 Drawing Sheets

APPARATUS FOR THE TREATMENT OF FLUIDS

FIELD OF THE INVENTION

The present invention relates to apparatus for the treatment of fluids. More particularly, the present invention relates to apparatus for effecting mass and/or heat transfer between fluids. Still more particularly, the present invention relates to apparatus for the treatment of fluids including cylindrical open ended housing closed by two end caps, each of which is provided with an inlet or an outlet for a first fluid intended to flow through a bundle of hollow fibers arranged within the cylindrical housing between two end walls.

BACKGROUND OF THE INVENTION

Various devices for the treatment of fluids and for effecting mass and/or heat transfer have been used, for example, for various types of medical treatments such as hemodialysis, hemofiltration, plasmaferesis and immunotherapy. Additional fields of use for such devices are, for example, dialysis and filtration in general, such as in connection with the cleaning or desalinization of seawater. Such apparatus according to the present invention may also be used as heat exchangers and/or blood oxygenators.

Such devices are generally disclosed in the art, for example, in U.S. Pat. Nos. 4,990,251 and 5,002,668, as well as European Patent No. 0,305,672 A1 and European Application No. 91.101006.4. Each of these patents, however, shows the use of inlets and outlets for the second fluid being arranged as nipples on the housing and provided with rather complicated tools for the manufacture of the housing.

U.S. Pat. No. 4,724,900, for example, describes an apparatus which has such inlets and outlets arranged in the end caps. A disadvantage of the design in this patent, however, is that the housing must be provided with openings in front of the inlets and outlets for one of the fluids. It is an object of the present invention to provide an improvement over these prior art devices.

SUMMARY OF THE INVENTION

In accordance with the present invention, these and other objects have now been achieved by the discovery of apparatus for the treatment of fluids which includes a cylindrical housing having a first open end, a second open end, and an inner wall surface, first and second end caps for closing the first and second open ends of the cylindrical housing, one of the first and second end caps including an inlet for the fluid and the other of the first and second end caps including an outlet for the fluid, a pair of end walls at the first and second ends of the cylindrical housing, a plurality of hollow fibers arranged longitudinally within the housing between the pair of end walls, at least one of the first and second end caps including outlet means for a second fluid whereby the second fluid can be withdrawn from the outer surface of the plurality of hollow fibers between the pair of end walls, and ring means mounted between the plurality of hollow fibers at the at least one of the first and second end caps so as to create a fluid channel for the second fluid between the ring means and the inner wall surface of the cylindrical housing.

The apparatus in accordance with the present invention can thus be used for effecting mass and/or heat transfer therein. By utilizing this invention, one can employ a very simple and inexpensive housing which can be manufactured either by injection molding or blow molding in simple forms or molds. Furthermore, handling of the housing is simplified in connection with the manufacturing of the complete apparatus. Other advantages will be set forth in the remainder of this specification.

In accordance with another embodiment of the apparatus of the present invention, the other of the first and second end caps includes inlet means for the second fluid for directing the second fluid to the outer surface of the plurality of hollow fibers. Such apparatus may therefore be used for dialysis and for filtration per se, or for the purification of sewage and the like. However, in connection with filtration, it is not necessary to have an inlet for the second fluid therein.

In accordance with a preferred embodiment of the apparatus of the present invention, the ring means is associated with one of the pair of end walls at the first end of the cylindrical housing. Preferably, the ring means is partially molded into that end wall. In order to obtain adequate sealing between the two fluids, which may be either liquids or gases, the ring means is preferably thus partially molded into the adjacent end wall.

In accordance with another embodiment of the apparatus of the present invention, the ring means includes an inner surface in contact with the plurality of hollow fibers and an outer surface. Preferably, the outer surface of the ring means is in contact with the inner wall of the first end cap. The ring means may also include duct means between its inner surface and its outer surface, whereby one of the pair of end walls may be molded within the duct means. Thus, in this embodiment, the ring means has an inner surface facing the fibers which is intended to support the fibers during molding of the adjacent end wall and an outer surface facing the housing and/or the end cap, and being supported by the housing and/or end cap. These inner and outer surfaces may thus be separated by one or more ducts which are filled with the molding material in connection with molding of the end walls. By employing this design, it is possible to obtain adequate sealing and at the same time distribution of the molding material is facilitated.

Since the channel or channels for the second fluid are arranged between the inner wall of the housing and the outer wall of the ring means, a rather simple design is attained, providing important advantages. That is, the end walls, which are normally made by molding polyurethane (PUR), but which can also be made from other such suitable materials, may be prevented from reaching the housing itself.

In accordance with another embodiment of the apparatus of the present invention, the ring means includes an inner surface in contact with the plurality of hollow fibers and an outer surface, and the inner surface of the ring means is substantially parallel and in line with the inner wall surface of the cylindrical housing, whereby the ring means and the inner wall surface of the cylindrical housing support the plurality of hollow fibers during molding of the pair of end walls.

In accordance with another embodiment of the apparatus of the present invention, the first and second end caps are attached to the cylindrical housing by means of gluing. Preferably, the first and second end caps are attached to the pair of end walls by gluing. Adequate sealing is also provided in this manner. Alternatively, however, the end caps may be attached by means of welding or by means of a screw connection. In connection with these alternatives, it may also be suitable to include further sealing means between the housing, the end caps and the end walls. Example of such sealing means will comprise sealing rings as shown in various prior art patents discussed above.

In accordance with another embodiment of the apparatus of the present invention, the first and second ends of the cylindrical housing include outwardly extending portions providing a portion of the fluid channel for the second fluid. Good distribution of the second fluid is provided thereby.

One significant advantage of the present invention is that the same housing may be combined with various types of end caps having different types of connection nipples for the connection of different types of tube connectors of tube types. Further advantages of the present invention include:

(1) optimal distribution of dialysate and other fluids around the bundle in the "head area" effected by the thickness, height and number of the fins provided by the housing, the end cap and the support ring;

(2) support of the bundle of hollow fibers before and during potting of the end walls; i.e., by variation of the inner diameter of the support ring means, it becomes possible to vary the diameter of the bundle of hollow fibers;

(3) the support ring transfers forces created, for example, by fiber shrinkage into the housing and thereby reduces the load on the glue seam between the end walls and the headers or end caps;

(4) all of the connectors may be placed at the headers;

(5) simple injection molding tools can be used for the housing;

(6) the same housing may be used for hemofiltration and hemodialyzers;

(7) a symmetrical housing is relatively easy to handle during production and assembly;

(8) no direct connection is required between the end walls and the housing;

(9) it is possible to recycle the housing; and

(10) the risk of cracks between the housing and the end walls is reduced, if not eliminated; i.e., such cracks are often created during steam sterilization of these devices.

BRIEF DESCRIPTION OF THE DRAWINGS

In order to more fully appreciate the following detailed description, reference can be made to the drawings, in which.

DETAILED DESCRIPTION

Figure 1:
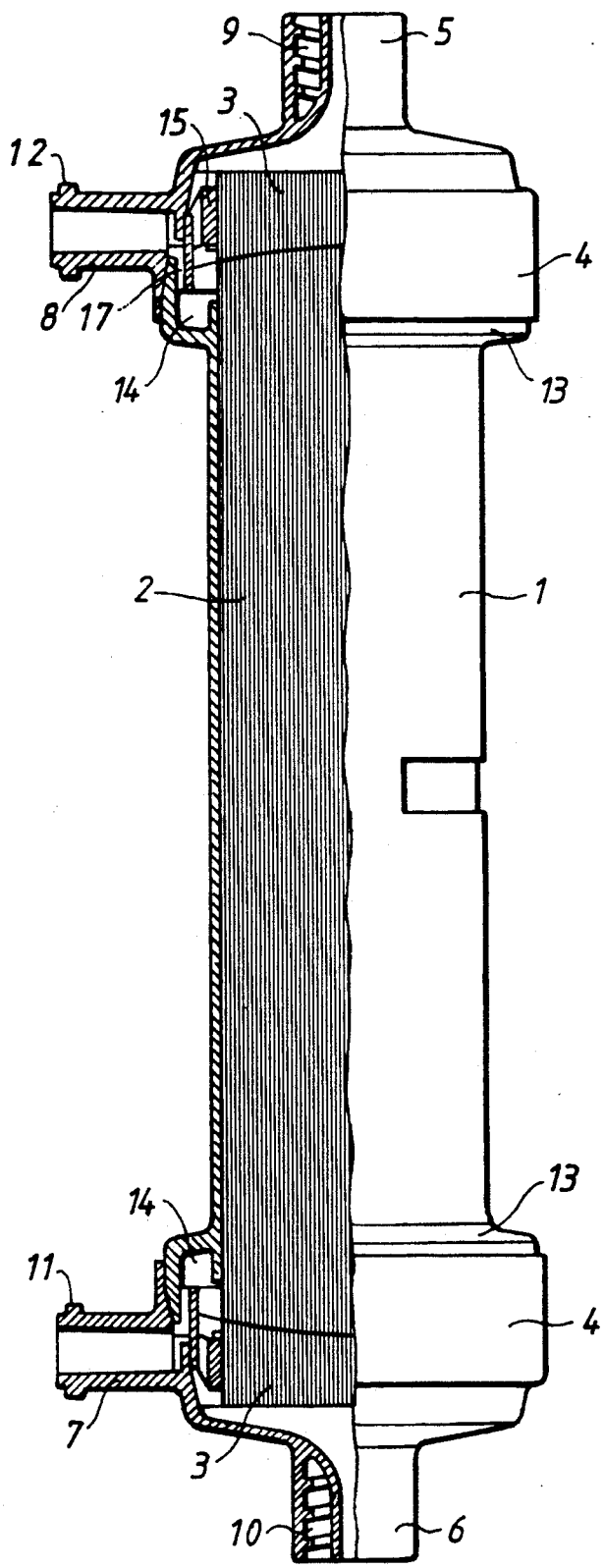
FIG. 1 is a side, elevational, partially sectional view of an apparatus in accordance with the present invention.

Referring to the Figures, in which like numerals refer to like portions thereof, FIG. 1 includes a housing 1 enclosing a bundle of hollow fibers 2, which are arranged between two end walls 3 of molded polyurethane or other suitable materials, as will be apparent to those skilled in this art. The ends of the open ended housing 1 are closed by two end caps 4, with an inlet 5 for a first fluid and an outlet 6 for the same fluid. The end caps 4 are, furthermore, provided with an inlet 7 for a second fluid and an outlet 8 for that fluid. The inlet 5 and the outlet 6 for the first fluid are provided with inner screw threads 9 and 10, respectively. The inlet 7 and the outlet 8 for the second fluid are instead provided with simple outer screw connections 11 and 12, respectively. The housing is provided at its end with a widened part 13, providing an inner peripheral channel 14. The polyurethane or other suitable material at the end walls 3 is prevented from reaching the housing 1 by a ring 15, which is shown in larger scale in FIG. 3.

Figure 2:
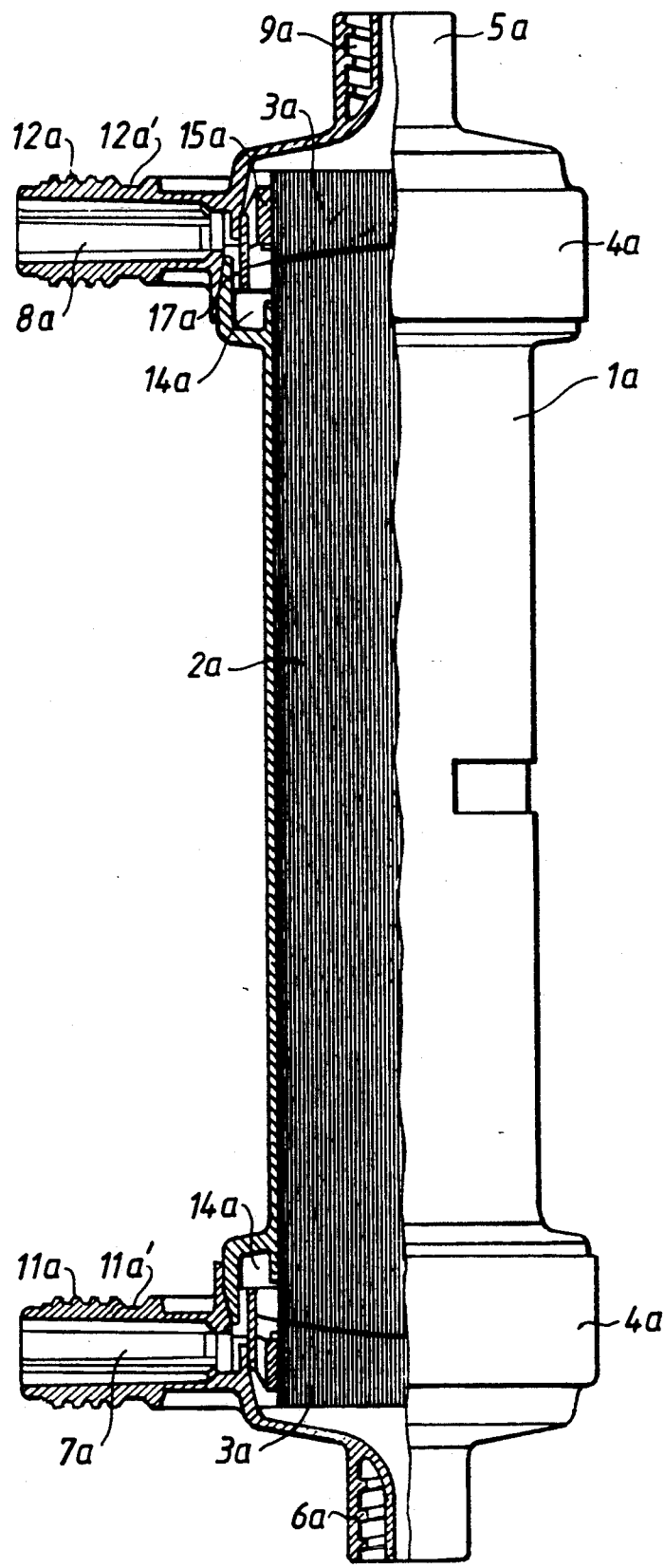
FIG. 2 is a side, elevational, partially sectional view of another embodiment of the apparatus in accordance with the present invention.

The embodiment shown in FIG. 2 corresponds essentially to the one shown in FIG. 1. The same reference numerals have therefore been used for corresponding details, but with the addition of a. The only difference is that in this case the inlet 7a and outlet 8a for the second fluid have been modified by being given more complete outer screw threads 11a and 12a, respectively. Inlet 7a and outlet 8a have furthermore been provided with grooves 11a' and 12a' respectively. By the combination of the screw threads 11a and 12a and the grooves 11a' and 12a', inlet 7a and outlet 8a may be used together with different kinds of tube connectors. This is described in more detail in European Patent Application No. 91.101006.4, filed Jan. 26, 1991. Screw threads 11a and 12a are intended to be used together with simple screw connectors, and grooves 11a' and 12a' are intended to be used together with more complicated connectors of the so-called Hansen type.

Figure 3:
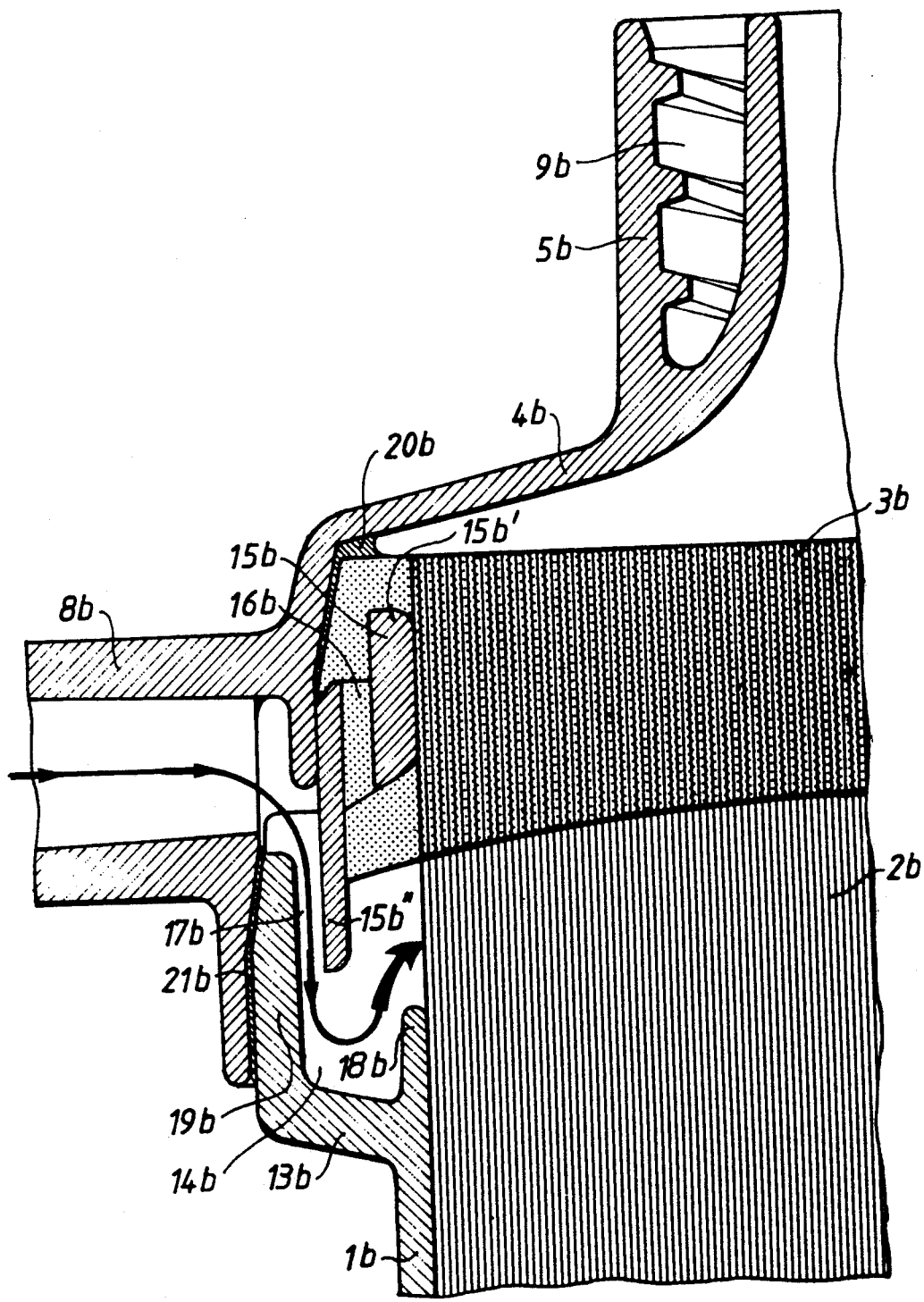
FIG. 3 is a side, elevational, partial, enlarged sectional view of a portion of another embodiment of the apparatus in accordance with the present invention.

The embodiment shown in FIG. 3 corresponds essentially to the embodiments shown in FIGS. 1 and 2. The same reference numerals have therefore been given to corresponding details, but with the addition of b. A bundle of hollow fibers 2b is arranged longitudinally in a housing 1b between two end walls 3b, of which only one is shown in the Figure. An inlet 5b for a first fluid is provided with an inner screw thread 9b. Nipple 8b is shown to be an inlet in this case. Consequently, the apparatus according to the invention may be designed either for co-current or a counter-current flow. Nipple 8b can also be provided with some type of tube connecting means. One possibility is, however, that a tube is pressed with a press fitting onto nipple 8b. The ring 15b is provided with an inner part 15b' and an outer part 15b'', which are themselves separated by one or more ducts 16b. Between the housing 1b and the ring 15b there is provided one or more channels 17b through which the second fluid may flow from the nipple 8b to the peripheral channel 14b, which is arranged between two flanges, 18b and 19b. Between the end cap 4b and the end wall 3b there is preferably a layer of glue 20b. A second layer of glue 21b is preferably arranged between the widened part 13b of the housing 1b and the end cap 4b. The attachment and the sealing may, however, also be provided, as mentioned above, by other means.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. Furthermore, for purposes of filtration, only one outlet is normally required for the second fluid. Any inlet for the second fluid is therefore not necessary for such use.

We claim:

1. Apparatus for the treatment of fluids comprising a cylindrical housing having a first open end, a second open end, and an inner wall surface, first and second end caps for closing said first and second open ends of said cylindrical housing, one of said first and second end caps including an inlet for said fluid, and said other of said first and second end caps including an outlet for said fluid, a pair of end walls at said first and second ends of said cylindrical housing, a plurality of hollow fibers arranged longitudinally within said housing between said pair of end walls, at least one of said first and second end caps including outlet means for a second fluid whereby said second fluid can be withdrawn from the outer surface of said plurality of hollow fibers between said pair of end walls, and ring means mounted between said plurality of hollow fibers and said inner wall surface at said at least one of said first and second end caps so as to create a fluid channel for said second fluid between said ring means and said inner wall surface of said cylindrical housing for optimal distribution of said second fluid.

2. The apparatus of claim 1 wherein said other of said first and second end caps includes inlet means for said second fluid for directing said second fluid to said outer surface of said plurality of hollow fibers.

3. The apparatus of claim 1 wherein said ring means is associated with one of said pair of end walls at said first end of said cylindrical housing.

4. The apparatus of claim 3 wherein said ring means is partially molded into said one of said pair of end walls.

5. The apparatus of claim 3 wherein said ring means includes an inner surface in contact with said plurality of hollow fibers and an outer surface.

6. The apparatus of claim 5 wherein said outer surface of said ring means is in contact with the inner wall of said first end cap.

7. The apparatus of claim 5 wherein said ring means includes duct means between said inner surface of said ring means and said outer surface of said ring means whereby said one of said pair of end walls may be molded within said duct means.

8. The apparatus of claim 1 wherein said ring means includes an inner surface in contact with said plurality of hollow fibers and an outer surface, and wherein said inner surface of said ring means is substantially parallel and in line with the inner wall surface of said cylindrical housing, whereby said ring means and said inner wall surface of said cylindrical housing support said plurality of hollow fibers during the molding of said pair of end walls.

9. The apparatus of claim 1 wherein said first and second end caps are attached to said cylindrical housing by means of gluing.

10. The apparatus of claim 9 wherein said first and second end caps are attached to said pair of end walls by gluing.

11. The apparatus of claim 1 wherein said first and second ends of said cylindrical housing include outwardly extending portions providing a portion of said fluid channel for said second fluid.

* * * * *